April 29, 1952 F. L. CALUYA Plant Pat. 1,090
ROSE PLANT
Filed Jan. 23, 1951
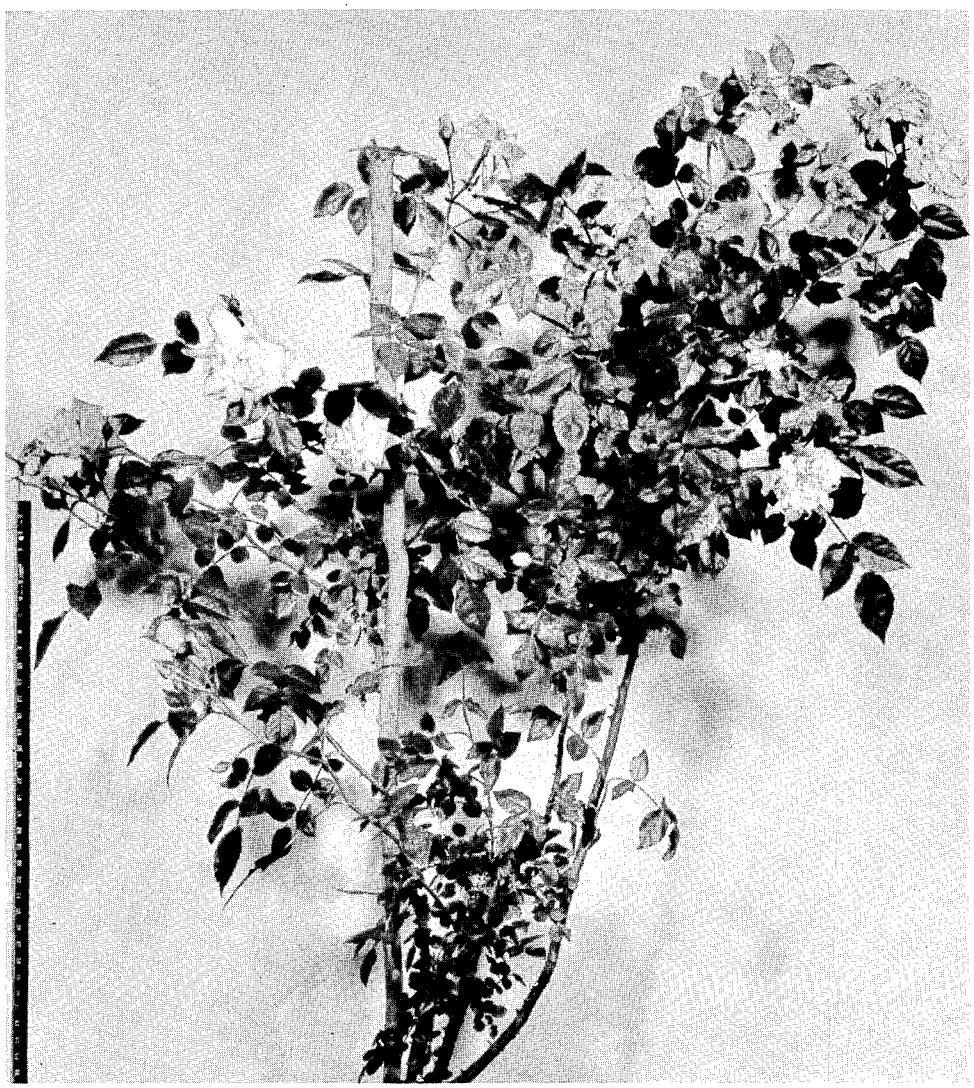
Inventor.
F. L. Caluya
By: Robert Cobb
Attorneys.

Patented Apr. 29, 1952

Plant Pat. 1,090

UNITED STATES PATENT OFFICE 1,090

ROSE PLANT

Frederick L. Caluya, Newman, Calif., assignor to Jackson & Perkins Company, Newark, N. Y., a corporation of New York Application January 23, 1951, Serial No. 207,420

1 Claim. (Cl. 47—61)

The present invention relates to a new and distinct variety of rose plant, originating as a sport of the well-known variety "Goldilocks" (Plant Patent No. 672), but dominantly distinguished therefrom by its climbing habit of growth. The new variety was discovered by me in a cultivated block of "Goldilocks" plants on property owned and controlled by my employer-assignee.

The parent variety is a floribunda bush rose which is primarily characterized by the exquisite golden yellow color and the long retention of this color throughout all stages of development of its flowers, and by its rugged habit of producing flowers under extreme conditions of heat and drought.

Of primary importance here, however, is the fact that this parent has never, so far as I am aware, exhibited a climbing habit, and its growth has been that of the average strong bush rose.

This new variety has the same general form and color of flower and foilage as its parent "Goldilocks," but sends up long, upright basal shoots from 6 to 7 feet tall the first year of growth, which shoots in turn send out lateral blooming spikes continuously throughout the summer, thus providing massive and repeating clusters of Empire Yellow bloom on the shoots and side branches through the entire summer, which is unusual in yellow climbing roses.

Aside from the distinguishing characteristics aforementioned, the new variety has the same characteristics that are present in the bush parent "Goldilocks," and it is therefore unnecessary to describe the plant in detail since it conforms to the description contained in Plant Patent No. 672, excepting only as to the bush habit of growth of the parent.

Asexual reproduction of the new variety by budding at Newark, New York, and at Pleasanton, California, shows that the foregoing characteristics come true to form and are established and transmitted through succeeding propagations.

The accompanying drawing shows a specimen plant of the new variety in comparison with an associated 36-inch scale or yardstick, relatively illustrating its climbing habit of growth.

I claim:

A new and distinct variety of rose plant of the climbing floribunda class, characterized as to novelty by its similarity to its parent "Goldilocks" (Plant Patent No. 672), but dominantly distinguished therefrom by its climbing habit of growth and by its habit of producing massive and repeating clusters of blooms on its long, upright basal shoots and on its side branches throughout the summer, substantially as shown and described herein.

FREDERICK L. CALUYA.

No references cited.